(12) United States Patent
Waldstreicher et al.

(10) Patent No.: US 6,352,997 B1
(45) Date of Patent: Mar. 5, 2002

(54) METHOD OF IMPROVING IN-VITRO FERTILIZATION

(75) Inventors: Joanne Waldstreicher, Scotch Plains; Georgianna S. Harris, Tinton Falls, both of NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/303,852

(22) Filed: May 3, 1999

Related U.S. Application Data

(62) Division of application No. 09/041,431, filed on Mar. 12, 1998, now Pat. No. 5,935,968.
(60) Provisional application No. 60/041,153, filed on Mar. 17, 1997.

(51) Int. Cl.$^7$ .......................... A61K 31/47; A61K 31/58
(52) U.S. Cl. ....................... 514/284; 544/318; 544/408; 546/77; 546/78; 546/14
(58) Field of Search ........................... 514/284; 546/14, 546/77, 78; 544/318, 408

(56) References Cited

U.S. PATENT DOCUMENTS

| | | | |
|---|---|---|---|
| 4,760,071 A | 7/1988 | Rasmusson et al. | 514/284 |
| 5,264,427 A | 11/1993 | Brodie et al. | 514/177 |
| 5,302,589 A | 4/1994 | Fry et al. | 514/210 |
| 5,359,071 A | 10/1994 | Durette et al. | 546/78 |
| 5,512,555 A | 4/1996 | Waldstreicher | 514/168 |
| 5,525,608 A | 6/1996 | Adams et al. | 514/284 |
| 5,543,406 A | 8/1996 | Andrews et al. | 514/213 |
| 5,543,417 A | 8/1996 | Waldstreicher | 514/284 |
| 5,547,957 A | 8/1996 | Gormley et al. | 514/284 |
| 5,565,467 A | 10/1996 | Batchelor et al. | 514/284 |
| 5,693,809 A | 12/1997 | Durette et al. | 546/77 |
| 5,696,266 A | 12/1997 | Humphrey et al. | 546/77 |
| 5,719,158 A | 2/1998 | Durette et al. | 514/284 |
| 5,739,137 A | 4/1998 | Durette et al. | 514/256 |
| 5,760,046 A | 6/1998 | Gormley et al. | 514/284 |
| 5,935,968 A * | 8/1999 | Waldstreicher | 514/284 |

FOREIGN PATENT DOCUMENTS

| WO | WO 94/14833 | 7/1994 |
|---|---|---|
| WO | WO 95/07926 | 3/1995 |

OTHER PUBLICATIONS

Stedmann's Medical Dictionary, 26th ed., Williams & Wilkins, Baltimore, USA, p. 799, 1995.*
Ciotta et al., Fertility & Sterility, vol. 64, No. 2, (1995), pp. 299–306, "Clinical and endocrine effects of finasteride, a 5–alpha–reductase inhibitor, in women with idiopathic hirsutism".
Stewart et al., The Lancet, vol.335, (1990), pp. 431–433, "5alpha–reductase activity in polycystic ovary syndrome".
Agarwal et al., J. Clin. Endoc. Metab., vol. 81 (1996), pp. 3686–3691, "A mechanism for the suppression of estrogen production in polycystic ovary syndrome".
Fruzzetti et al., J. Clin. Endoc. Metab., vol. 79 (1994), pp. 831–835, Effects of finasteride, a 5–alpha–reductase inhibitor, on circulating androgens and gonadotropin secretion in hirsute.

Haning Jr., et al., J. Steroid Biochem. Molec. Biol., vol. 59, (1996), pp. 199–204, 5alpha–reductase 1 and 2 expression and activity in human ovarian follicles, stroma and . . . .
Rodin et al., N. Engl. J. of Med., (1994), vol. 330, pp. 460–465, "Hyperandrogenism in polycystic ovary syndrome".
Tolino et al., Fertility and Sterility, vol. 66, No. 1, (1996), p. 61–65, "Finasteride in the treatment of hirsutism: New therapeutic perspectives".
Ehrmann et al., Endocrine Reviews, vol. 16 (1995), pp. 322–352, "Polycystic ovary syndrome as a form of functional ovarian hyperandrogenism due to dysregulation of anddrogen secretion".
Erickson et al., The Ovary, (1993), Chapter 28, pp. 561–579, "The Polycystic Ovary Syndrome".
Wong et al., J. Clin. Endoc. Metab., vol. 80 (1995), pp. 233–238, "A prospective randomized trial comparing finasteride to spironolactone in the treatment of hirsute women".
Moghetti et al., J. Clin. Endoc. Metab., vol. 79 (1994), pp. 1115–1121, "Clinical and hormonal effects of the 5alpha–reductase inhibitor finasteride in idiopathic hirsutism".
Rittmaster, Lancet, vol. 349 (1997), pp. 191–195, "Hitsutism".
Castello et al., Fertility and Sterility, vol. 66 (1996), pp. 734–740, "Outcome of long–term treatmentwith the 5alpha–reductase inhibitor finasteride in idiopathic hirsutism . . . ".

* cited by examiner

*Primary Examiner*—F. T. Moezie
(74) *Attorney, Agent, or Firm*—Catherine D. Fitch; Melvin Winokur

(57) ABSTRACT

The present invention provides for a method of treating polycystic ovary syndrome in a subject in need of such treatment comprising the administration of a therapeutically effective amount of a compound of structural formula I:

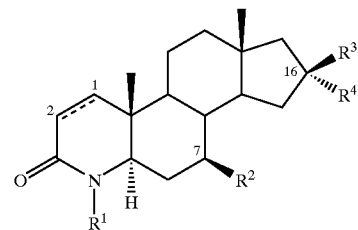

to the subject. The present invention further provides for a method for improving fertility and the response to in vitro fertilization (I.V.F.), comprising administration of therapeutically effective amount of compound of structural formula I to the subject. Further, the present invention provides for compositions useful in the methods of the present invention, as well as a method of manufacture of a medicament useful for treating polycystic ovary syndrome or for improving fertility or the response to in vitro fertilization (I.V.F.).

6 Claims, No Drawings

METHOD OF IMPROVING IN-VITRO FERTILIZATION

CROSS-REFERENCE TO RELATED APPLICATIONS

The present application is a divisional application of U.S. Ser. No. 09/041,431, filed Mar. 12, 1998 now U.S. Pat. No. 5,935,968, which in turn claims the benefit provisional application U.S. Ser. No. 60/041,153, filed Mar. 17, 1997.

BACKGROUND OF THE INVENTION

The present invention provides for a novel method of treating polycystic ovary syndrome. Further, the present invention is directed to a method of improving fertility and the response to in vitro fertilization (I.V.F.) by employing a 5α-reductase type 1 inhibitor. The present invention also provides for a method of manufacture of a medicament useful for treating polycystic ovary syndrome and a method of manufacture of a medicament useful as an adjunct in I.V.F. The present invention also provides for compositions useful in the method of treating polycystic ovary syndrome and useful as an adjunct in I.V.F.

Polycystic ovary syndrome (PCOS), also known as Stein-Leventhal syndrome, is characterized by menstrual irregularity and hirsutism and is a common cause of anovulatory infertility. The biochemical abnormalities are a high concentration of plasma luteinising hormone (LH) or a high LH/follicle stimulating hormone (FSH) ratio and high concentrations of androgens (testosterone and/or androstenedione and/or dehydroepiandrosterone (DHEA)). The increased androgens can be secreted by the ovary and/or the adrenal gland. Clinical manifestations of PCOS include amenorrhea, hirsutism acanthosis nigricans, acne and obesity. PCOS appears to account for about 75% of anovulatory infertility.

The chronic anovulation typical of PCOS results in an increased number of atretic follicles (which become cysts) and increased interstitial tissue in the stroma of the ovaries.

Under normal conditions, women produce a single dominant follicle that participates in a single ovulation each menstrual cycle. The process begins when a cohort of primordial follicles is recruited to initiate growth. Successive recruitment gives rise to the primary, secondary, tertiary and graafian follicles present in the ovaries. The ability to become a dominant follicle is not a characteristic shared by all follicles, and those that lack the property die by atresia due to increased androgens. In the human female, only about 400 of the original 7 million follicles survive atresia and give rise to dominant follicles.

In patients with PCOS, the process of folliculogenesis does not proceed normally. The initial steps, recruitment and growth to the small graafian stages, are functioning in PCOS, but the terminal step, the selection of dominant follicles that can ovulate, does not occur regularly. Viable follicles seldom develop beyond about the 6 mm stage. In some unexplained way, this condition leads to the accumulation of large numbers of small graafian follicles (commonly referred to as cysts) in which the theca interstitial cells (TIC) produce abnormally large amounts of androgen, but the granulosa cells (GC) fail to express the aromatase enzyme and aromatize the androgen substrate to estradiol. Consequently, a state of continued hyperandrogenism results. The problem is self-perpetuating in part because the atretic follicle becomes an androgenic follicle by a "default" mechanism: because of low aromatase activity in atretic follicles, androstenedione is preferentially metabolized to testosterone and thence to dihydrotestosterone within the ovary.

The human ovarian stromal, thecal and granulosa cell compartments each contain 5α-reductase activity. In the rat the 5α-reduced androgens 5α-androstane-3,17-dione (5α-A) and dihyrotestosterone (DHT) are competitive inhibitors of aromatase activity. This is likely to occur in humans as well, and therefore the 5α-reduced metabolites may lead to decreased aromatase activity, increased androgen secretion and follicular atresia.

Agarwal et al. "A Mechanism for the Suppression of Estrogen Production in Polycystic Ovary Syndrome" J. Clin Endocrinology & Metabolism 81(10):3686–3691 (1996), propose that polycystic ovary syndrome follicular fluid contains abnormally high 5α-A and/or DHT concentration that can inhibit aromatase activity. They conclude that 5α-A is the primary inhibitor of aromatase activity in PCOS follicular fluid.

Stewart et al. "5α-reductase adtivity in polycystic ovary syndrome" The Lancet 335:431–433 (1990) investigated the hypothesis that in PCOS increased cortisol metabolism stimulates corticotropin-mediated androgen excess. They proposed that enhanced activity of 5α-reductase is the fundamental defect in many patients with PCOS. The enzyme abnormality is proposed to mediate both hirsutism and enhanced hepatic cortisol metabolism. A concomitant increase in corticotropin secretion in women with PCOS is hypothesized to keep plasma cortisol concentrations normal, but at the expense of androgen excess. This hypothesis likely provides another mechanism, via the adrenal, in which the 5α-reductase activity contributes to PCOS.

Presently polycystic ovary syndrome is treated with GnRH analogues, oral contraceptives, steroids (such as prednisone) and/or antiandrogens. These antagonize androgens or decrease the whole H-P-G or H-P-Adrenal axes. None of the treatments currently employed corrects the underlying problem of the hyperandrogenic production by the ovarian follicles. Further, each of the currently employed treatments has significant side effects including: hypoestrogenism (GnRH analogues), menstrual irregularity (spironolactone, an antiandrogen), and headaches, bloating and the rare occurrence of blood clots associated with oral contraceptives. Steroids also have significant side effects such as adrenal suppression, obesity, striae, hypertension, etc.

The present invention relates to methods of treating polycystic ovary syndrome. Further, the present invention is directed to a method of improving fertility and the response to in vitro fertilization (I.V.F.) by employing a 5α-reductase type 1 inhibitor. It has now been found that a 5α-reductase type 1 inhibitors of structural formula I:

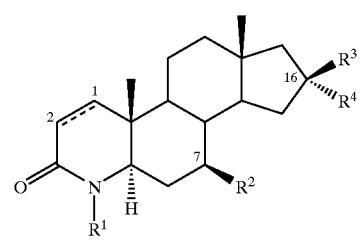

are useful for the treatment of polycystic ovary syndrome and for improving fertility and the response to in vitro fertilization.

The enzyme 5α-reductase catalyzes the reduction of several androgens including: testosterone (T) to the more potent androgen, 5α-dihydrotestosterone (dihydrotestosterone" or DHT), as shown below:

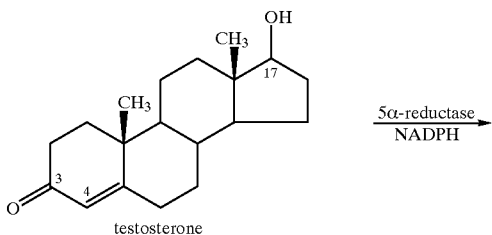

testosterone

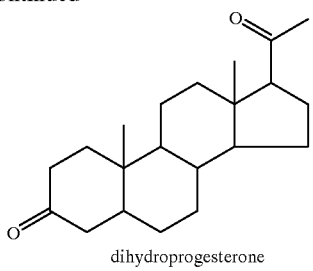

dihydrotestosterone

5α-reductase also catalyzes the reduction of androstenedione (A) to androstanedione (5α-A), as shown below:

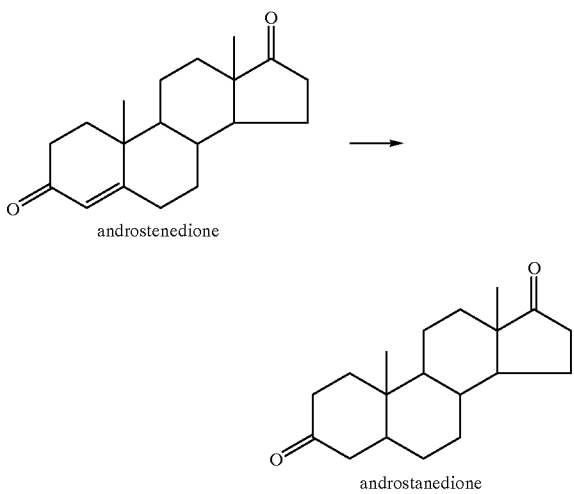

and the reduction of progesterone to dihydroprogesterone, as shown below:

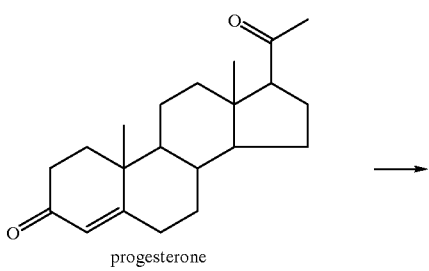

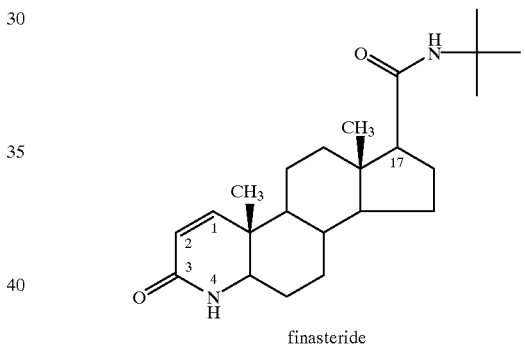

dihydroprogesterone

There are two isozymes of 5α-reductase in humans. Andersson, et al., Proc. Natl. Acad. Sci. USA, 87:3640–44 (1990); Andersson, et al., Nature, 354, 159–61 (1991). The isozymes, usually called Type 1 and Type 2, exhibit differences in their biochemical properties, genetics, and pharmacology. Both isozymes are now the subject of considerable research and it has been found one isozyme (type 1) predominates in the sebaceous glands of facial skin and skin tissue and that the other (type 2) predominates in the prostate.

Finasteride (17β-(N-tert-butylcarbamoyl)-3-oxo-4-aza-5α-androst-1-en-3-one) as shown below, is a potent inhibitor of the human type 2 enzyme.

finasteride

Under the tradename PROSCAR®, finasteride is known to be useful in the treatment of hyperandrogenic conditions, see e.g., U.S. Pat. No. 4,760,071. Finasteride is currently prescribed for the treatment of benign prostatic hyperplasia (BPH), a condition affecting to some degree the majority of men over age 55. Finasteride's usefulness in the treatment of androgenic alopecia and prostatic cancer is described in the following documents: EP 0 285 382, published Oct. 5, 1988, EP 0 285 383, published Oct. 5, 1988 and Canadian patents 1,302,277 and 1,302,276.

There have been reports (e.g., Ciotta et al., Fertility & Sterility 64(2): 299–306,1996 and Fruzetti et al., J. Clin. Endocrin. Metab. 79: 703–706, 1994) in the literature of administration of the type 2 inhibitor finasteride to women with hirsutism, with no observed menstrual changes. Further, it has been reported that women with type 2 5α-reductase deficiency have normal menstrual cycles. This suggests that the type 2 enzyme does not predominate in the ovary.

Haning, Jr., et al., J. Steroid Molec. Biol. 59(2): 199–204 (1996) have recently reported that the human ovary apparently expresses mRNA for 5α-reductase type 1.

It has been presently found that the type 1 5α-reductase inhibitors of the present invention are useful in the treatment

SUMMARY OF THE INVENTION

The present invention provides for a method of treating polycystic ovary syndrome in a subject in need of such treatment comprising the administration of a therapeutically effective amount of a compound of structural formula I:

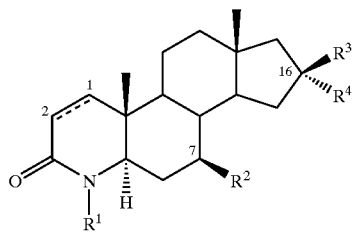

to the subject. The present invention further provides for a method for improving fertility and the response to in vitro fertilization (I.V.F.), comprising administration of therapeutically effective amount of compound of structural formula I to the subject. Further, the present invention provides for compositions useful in the methods of the present invention, as well as a method of manufacture of a medicament useful for treating polycystic ovary syndrome or for improving fertility and the response to in vitro fertilization (I.V.F.).

DETAILED DESCRIPTION OF THE INVENTION

In one embodiment, the present invention is directed to a method for treating polycystic ovary syndrome in a subject in need thereof by administering to the subject an effective amount of a compound of structural formula I:

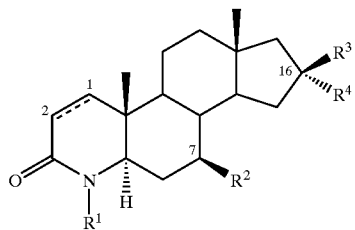

or a pharmaceutically acceptable salt or ester thereof wherein:

the C1–C2 carbon-carbon bond may be a single bond, or a double bond as indicated by the dashed line;

$R^1$ is selected from the group consisting of hydrogen and $C_{1-10}$ alkyl;

$R^2$ is selected from the group consisting of hydrogen and $C_{1-10}$ alkyl; one of $R^3$ and $R^4$ is selected from the group consisting of hydrogen and methyl, and the other is selected from the group consisting of:
(a) amino;
(b) cyano;
(c) fluoro;
(d) methyl;
(e) OH;
(f) —C(O)NR$_b$R$_c$, where R$_b$ and R$_c$ are independently H, $C_{1-6}$ alkyl, aryl, or arylC$_{1-6}$ alkyl; wherein the alkyl moiety can be substituted with 1–3 of: halo; $C_{1-4}$ alkoxy; or trifluoromethyl; and the aryl moiety can be substituted with 1–3 of: halo; $C_{1-4}$ alkyl; $C_{1-4}$ alkoxy; or trifluoromethyl;
(g) $C_{1-10}$ alkyl-X—;
(h) $C_{2-10}$ alkenyl-X—;
wherein the $C_{1-10}$ alkyl in (g) and $C_{2-10}$ alkenyl in (h) can be unsubstituted or substituted with one to three of:
  i) halo; hydroxy; cyano; nitro; mono-, di- or trihalomethyl; oxo; hydroxysulfonyl; carboxy;
  ii) hydroxyC$_{1-6}$ alkyl; $C_{1-6}$ alkyloxy; $C_{1-6}$ alkylthio; $C_{1-6}$ alkylsulfonyl; $C_{1-6}$ alkyloxycarbonyl; in which the $C_{1-6}$ alkyl moiety can be further substituted with 1–3 of: halo; $C_{1-4}$ alkoxy; or trifluoromethyl;
  iii) arylthio; aryl; aryloxy; arylsulfonyl; aryloxycarbonyl; in which the aryl moiety can be further substituted with 1–3 of: halo; $C_{1-4}$ alkyl; $C_{1-4}$ alkoxy; or trifluoromethyl;
  iv) —C(O)NR$_b$R$_c$; —N(R$_b$)—C(O)—R$_c$; —NR$_b$R$_c$; where R$_b$ and R$_c$ are defined above;
(i) aryl-X—;
(j) heteroaryl-X—, wherein heteroaryl is a 5, 6 or 7 membered heteroaromatic ring containing at least one member selected from the group consisting of: one ring oxygen atom, one ring sulfur atom, 1–4 ring nitrogen atoms, or combinations thereof, in which the heteroaromatic ring can also be fused with one benzo or heteroaromatic ring; wherein the aryl in (i) and heteroaryl in (j) can be unsubstituted or substituted with one to three of:
  v) halo; hydroxy; cyano; nitro; mono-, di- or trihalomethyl; mono-, di- or trihalomethoxy; $C_{2-6}$ alkenyl; $C_{3-6}$ cycloalkyl; formyl; hydrosulfonyl; carboxy; ureido;
  vi) $C_{1-6}$ alkyl; hydroxy $C_{1-6}$ alkyl; $C_{1-6}$ alkyloxy; $C_{1-6}$ alkyloxy $C_{1-6}$ alkyl; $C_{1-6}$ alkylcarbonyl; $C_{1-6}$ alkylsulfonyl; $C_{1-6}$ alkylthio; $C_{1-6}$ alkylsulfinyl; $C_{1-6}$ alkylsulfonamido; $C_{1-6}$ alkylarylsulfonamido; $C_{1-6}$ alkyloxy-carbonyl; $C_{1-6}$ alkyloxycarbonyl $C_{1-6}$ alkyl; R$_b$R$_c$N—C(O)—$C_{1-6}$ alkyl; $C_{1-6}$ alkanoylamino $C_{1-6}$ alkyl; aroylamino $C_{1-6}$ alkyl; wherein the $C_{1-6}$ alkyl moiety can be substituted with 1–3 of: halo; $C_{1-4}$ alkoxy; or trifluoromethyl;
  vii) aryl; aryloxy; arylcarbonyl; arylthio; arylsulfonyl; arylsulfinyl; arylsulfonamido; aryloxycarbonyl; wherein the aryl moiety can be substituted with 1–3 of: halo; $C_{1-4}$ alkyl; $C_{1-4}$ alkoxy; or trifluoromethyl;
  viii) —C(O)NR$_b$R$_c$; —O—C(O)—NR$_b$R$_c$; —N(R$_b$)—C(O)—R$_c$; —NR$_b$R$_c$; R$_b$—C(O)—N(R$_c$)—; where R$_b$ and R$_c$ are defined in (f) above; and —N(R$_b$)—C(O)—OR$_g$, wherein R$_g$ is $C_{1-6}$ alkyl or aryl, in which the alkyl moiety can be substituted with 1–3 of: halo; $C_{1-4}$ alkoxy; or trifluoromethyl, and the aryl moiety can be substituted with 1–3 of: halo; $C_{1-4}$ alkyl; $C_{1-4}$ alkoxy, or trifluoromethyl; —N(R$_b$)—C(O)NR$_c$R$_d$, wherein R$_d$ is selected from H, $C_{1-6}$ alkyl, and aryl; in which said $C_{1-6}$ alkyl and aryl can be substituted as described above in (f) for R$_b$ and R$_c$;
  ix) a heterocyclic group, which is a 5, 6 or 7 membered ring, containing at least one member selected from the group consisting of: one ring oxygen atom, one ring sulfur atom, 1–4 ring nitrogen atoms, or combinations thereof; in which the heterocyclic ring can be aromatic, unsaturated, or saturated, wherein the heterocyclic ring can be fused with a benzo ring, and wherein said heterocyclic ring can be substituted with one to three substituents, as defined above for v), vi), vii) and viii), excluding ix) a heterocyclic group; and (k) $R^3$ and $R^4$ taken together can be carbonyl oxygen;

(l) $R^3$ and $R^4$ taken together can be =CH—$R_g$, wherein $R_g$ is defined in viii); and wherein:

X is selected from the group consisting of:
—O—; —S(O)$_n$—; —C(O)—; —CH($R_e$)—; —C(O)—O—*; —C(O)—N($R_e$)—*; —N($R_e$)—C(O)—O—*; —O—C(O)—N($R_e$)—*; —N($R_e$)C(O)—N($R_e$)—; —O—CH($R_e$)—*; —N($R_e$)—;
wherein $R_e$ is H, $C_{1-3}$ alkyl, aryl, aryl-$C_{1-3}$ alkyl, or unsubstituted or substituted heteroaryl, as defined above in (j);

wherein the asterisk (*) denotes the bond which is attached to the 16-position in Structure I; and n is zero, 1 or 2.

Still a further aspect of the present invention is a method of improving fertility and the response to in vitro fertilization (I.V.F.), in a subject in need thereof by administering an effective amount of a compound of structural formula I to the subject. The compounds of the present invention may provide a useful adjunct for in vitro fertilization because they may lead to multiple ovarian follicles developing completely through ovulation.

Another aspect of the present invention is the use of a compound of structural formula I for the manufacture of a medicament useful to treat polycystic ovary syndrome in a subject in need thereof. Still a further aspect of the present invention is the use of a compound of structural formula I for the manufacture of a medicament useful to improve fertility and the response to in vitro fertilization in a subject in need thereof.

In one embodiment of the present invention compounds of structural Formula I wherein $R^1$ is hydrogen or methyl.

In another embodiment of the present invention, $R^2$ is hydrogen or methyl.

A further embodiment of the present invention employs compounds of Formula I wherein:

one of $R^3$ and $R^4$ is selected from the group consisting of hydrogen and methyl, and the other is selected from the group consisting of:
(b) cyano;
(c) fluoro;
(e) OH;
(g) $C_{1-10}$ alkyl-X—; or $C_{1-10}$ alkyl-X—, where alkyl can be substituted with aryl, and wherein aryl in turn can be substituted with 1–2 of halo or $C_{1-6}$ alkyl;
(h) $C_{2-10}$ alkenyl-X;
(i) aryl-X—;
(j) heteroaryl-X—, wherein heteroaryl is a 5 or 6 membered heteroaromatic ring containing 1–2 ring nitrogen atoms; wherein the aryl in (i) and heteroaryl in (j) can be unsubstituted or substituted with one to two of:
x) halo; cyano; nitro; trihalomethyl; trihalomethoxy; $C_{1-6}$ alkyl; aryl; $C_{1-6}$ alkylsulfonyl; $C_{1-6}$ alkyl-arylsulfonamino;
xi) —NR$_b$R$_c$; R$_b$—C(O)—N(R$_c$)—; wherein R$_b$ and R$_c$ are independently H, $C_{1-6}$ alkyl, aryl, or arylC$_{1-6}$ alkyl; wherein the alkyl moiety can be substituted with 1–3 of: halo; $C_{1-4}$ alkoxy; or trifluoromethyl; and the aryl moiety can be substituted with 1–3 of: halo; $C_{1-4}$ alkyl; $C_{1-4}$ alkoxy; or trifluoromethyl;
xii) a heterocyclic group, which is a 5 membered aromatic ring, containing one ring nitrogen atom, or one ring oxygen and one ring nitrogen atom; and (k) wherein $R^3$ and $R^4$ taken together can be carbonyl oxygen.

In a further embodiment of the present invention, X is selected from the group consisting of:
—O—; —S(O)$_n$—; —CH($R_e$)—; —C(O)—N($R_e$)—*; —O—C(O)—N($R_e$)—*;

wherein the asterisk (*) denotes the bond which is attached to the 16-position in Structure I; and n is zero or 2.

In another embodiment of the present invention, $R_e$ is H, $C_{1-3}$ alkyl, aryl, or aryl $C_{1-3}$ alkyl.

Compounds of Formula I which may be employed in the present invention include but are not limited to the following:

4-aza-4,7β-dimethyl-5α-androstane-3,16-dione;

4-aza-4-methyl-5α-androstan-3,16-dione;

3-oxo-4-aza-4-methyl-16β-hydroxy-5α-androstane;

3-oxo-4-aza-4-methyl-16β-(benzylaminocarbonyloxy)-5α-androstane;

3-oxo-4-aza-4-methyl-16-benzoylamino-5α-androstane;

3-oxo-4-aza-4-methyl-16-methoxy-5α-androstane;

3-oxo-4-aza-4-methyl-16β-allyloxy-5α-androstane;

3-oxo-4-aza-4-methyl-16β-(n-propyloxy)-5α-androstane;

3-oxo-4-aza-4-methyl-16α-hydroxy-5α-androstane;

3-oxo-4-aza-4-methyl-16β-(phenoxy)-5α-androstane;

3-oxo-4-aza-7β-methyl-16β-(phenoxy)-5α-androst-1-ene;

3-oxo-4-aza-4-methyl-16α-methoxy-5α-androstane;

3-oxo-4-aza-4-methyl-16β-(4-chlorophenoxy)-5α-androstane;

3-oxo-4-aza-7β-methyl-16β-(4-chlorophenoxy)-5α-androst-1-ene;

3-oxo-4-aza-7β-methyl-16β-(4-chlorophenoxy)-5α-androstane;

3-oxo-4-aza-7β-methyl-16β-(3-chloro-4-methylphenoxy)-5α-androstane;

3-oxo-4-aza-7β-methyl-16β-(4-methylphenoxy)-5α-androstane;

3-oxo-4-aza-7β-methyl-16β-(4-methylphenoxy)-5α-androst-1-ene;

3-oxo-4-aza-7β-methyl-16β-[4-(1-pyrrolyl)phenoxy]-5α-androst-1-ene;

3-oxo-4-aza-4,7β-dimethyl-16β-hydroxy-5α-androstane;

3-oxo-4-aza-4,7β-dimethyl-16β-methoxy-5α-androstane;

3-oxo-4-aza-4,7β-dimethyl-16β-allyloxy-5α-androstane;

3-oxo-4-aza-4,7β-dimethyl-16β-(3,3-dimethylallyloxy)-5α-androstane;

3-oxo-4-aza-4,7β-dimethyl-16β-(n-propyloxy)-5α-androstane;

3-oxo-4-aza-4,7β-dimethyl-16β-(iso-pentoxy)-5α-androstane;

3-oxo-4-aza-4,16α-dimethyl-16β-hydroxy-5α-androstane;

3-oxo-4-aza-4,7β-dimethyl-16β-ethyloxy-5α-androstane;

3-oxo-4-aza-4,7β-dimethyl-16β-benzyloxy-5α-androstane;

3-oxo-4-aza-4,7β-dimethyl-16α-hydroxy-5α-androstane;
3-oxo-4-aza-4,7β-dimethyl-16β-methylthio-5α-androstane;
3-oxo-4-aza-4,7β-dimethyl-16β-(n-propylthio)-5α-androstane;
3-oxo-4-aza-4,7β-dimethyl-16β-fluoro-5α-androstane;
3-oxo-4-aza-4,7β-dimethyl-16β-cyano-5α-androstane;
3-oxo-4-aza-4-methyl-16β-(1-hexyl)-5α-androstane;
3-oxo-4-aza-4,7β-dimethyl-16β-(n-propyl)-5α-androstane;
3-oxo-4-aza-4,7β-dimethyl-16β-benzyl-5α-androstane;
3-oxo-4-aza-4,7β-dimethyl-16β-(4-chlorobenzyl)-5α-androstane;
3-oxo-4-aza-4,16α-dimethyl-16β-methoxy-5α-androstane;
3-oxo-4-aza-4,7β-dimethyl-16β-(4-cyanophenoxy)-5α-androstane;
3-oxo-4-aza-4,7β-dimethyl-16β-(3-cyanophenoxy)-5α-androstane;
3-oxo-4-aza-4,7β-dimethyl-16β-(4-nitrophenoxy)-5α-androstane;
3-oxo-4-aza-4,7β-dimethyl-16β-(1-naphthyloxy)-5α-androstane;
3-oxo-4-aza-4,7β-dimethyl-16β-(3-chloro-4-methylphenoxy)-5α-androstane;
3-oxo-4-aza-4,7β-dimethyl-16β-(4-methylphenoxy)-5α-androstane;
3-oxo-4-aza-4,7β-dimethyl-16β-(tert-butyloxy)-5α-androstane;
3-oxo-4-aza-4,7β-dimethyl-16β-(3-methyl-1-butyloxy)-5α-androstane;
3-oxo-4-aza-4,7β-dimethyl-16α-(n-propyloxy)-5α-androstane;
3-oxo-4-aza-4,7β-dimethyl-16β-(4-trifluoromethylphenoxy)-5α-androstane;
3-oxo-4-aza-4,7β-dimethyl-16β-(4-trifluoromethoxyphenoxy)-5α-androstane;
3-oxo-4-aza-4,7β-dimethyl-16β-ethylthio-5α-androstane;
3-oxo-4-aza-4,7β-dimethyl-16β-ethylsulfonyl-5α-androstane;
3-oxo-4-aza-4,7β-dimethyl-16β-(4-methylsulfonylphenoxy)-5α-androstane;
3-oxo-4-aza-4,7β-dimethyl-16β-[4-(4-tolylsulfonylamino)phenoxyl]-5α-androstane;
3-oxo-4-aza-4,7β-dimethyl-16β-(3-pyridyloxy)-5α-androstane;
3-oxo-4-aza-4,7β-dimethyl-16β-[(4-phenyl)phenoxy)-5α-androstane;
3-oxo-4-aza-4,7β-dimethyl-16β-(4-fluorophenoxy)-5α-androstane;
3-oxo-4-aza-4,7β-dimethyl-16β-(2-pyrazinyloxy)-5α-androstane;
3-oxo-4-aza-4,7β-dimethyl-16β-[4-(5-oxazolyl)phenoxy]-5α-androstane;
3-oxo-4-aza-4,7β-dimethyl-16β-(2-pyrimidinyloxy)-5α-androstane;
3-oxo-4-aza-4,7β-dimethyl-16β-[4-(1-pyrryl)phenoxy]-5α-androstane;
3-oxo-4-aza-4,7β-dimethyl-16β-(4-aminophenoxy)-5α-androstane;
3-oxo-4-aza-4,7β-dimethyl-16β-(4-acetylaminophenoxy)-5α-androstane;
3-oxo-4-aza-4,7β-dimethyl-16β-(4-benzoylaminophenoxy)-5α-androstane;
3-oxo-4-aza-4,7β-dimethyl-16β-(4-chlorophenoxy)-5α-androstane;
3-oxo-4-aza-4,7β-dimethyl-16β-(phenoxy)-5α-androstane;
3-oxo-4-aza-4,7β-dimethyl-16β-(2-chlorophenoxy)-5α-androstane;
3-oxo-4-aza-4,7β-dimethyl-16β-(3-chlorophenoxy)-5α-androstane;
3-oxo-4-aza-4,7β-dimethyl-16β-(4-chlorophenoxy)-5α-androst-1-ene;
3-oxo-4-aza-4,7β-dimethyl-16-(4-chlorobenzylidene)-5α-androstane;
3-oxo-4-aza-4,7β-dimethyl-16-benzylidene-5α-androstane;
3-oxo-4-aza-4,7β-dimethyl-16-(4-methylbenzylidene)-5α-androstane;
3-oxo-4-aza-4,7β-dimethyl-16-(4-chlorobenzyl)-5α-androstane;
3-oxo-4-aza-4,7β-dimethyl-16-(4-methylbenzyl)-5α-androstane;
3-oxo-4-aza-4,7β-dimethyl-16-(3-pyridylmethyl)-5α-androstane;
3-oxo-4-aza-4,7β-dimethyl-16α-methanesulfonyl-5α-androstane;
3-oxo-4-aza-4,7β-dimethyl-16β-thiophenoxy-5α-androstane;
3-oxo-4-aza-4,7β-dimethyl-16β-(4-chlorothiophenoxy)-5α-androstane;
3-oxo-4-aza-4,7β-dimethyl-16β-(4-fluorothiophenoxy)-5α-androstane;
3-oxo-4-aza-4,7β-dimethyl-16β-(4-methylthiophenoxy)-5α-androstane;
3-oxo-4-aza-4,7β-dimethyl-16β-(4-methoxythiophenoxy)-5α-androstane;
3-oxo-4-aza-4,7β-dimethyl-16β-phenylsulfinyl-5α-androstane;
3-oxo-4-aza-4,7β-dimethyl-16β-phenylsulfonyl-5α-androstane;
3-oxo-4-aza-4,7β,16α-trimethyl-16β-(4-trifluoromethylphenoxy)-5α-androstane;
3-oxo-4-aza-4,7β,16α-trimethyl-16β-hydroxy-5α-androstane;
3-oxo-4-aza-4,7β,16α-trimethyl-16β-methoxy-5α-androstane; pharmaceutically acceptable salts thereof, and analogs of the above-described compounds wherein the C1–C2 carbon-carbon bond is a double bond, and/or $R^1$ is —H, and/or $R^2$ is —H or methyl, where appropriate.

In another embodiment of compounds of Formula I are those further limited to those wherein the $C_1$–$C_2$ carbon-carbon bond is a single bond, $R^1$ is methyl, $R^2$ is methyl, $R^3$ is selected from unsubstituted or substituted aryloxy, and $R^4$ is hydrogen.

Some non-limiting examples of compounds of Formula I within this embodiment are:
3-oxo-4-aza-4,7β-dimethyl-16β-(4-cyanophenoxy)-5α-androstane;
3-oxo-4-aza-4,7β-dimethyl-16β-(3-cyanophenoxy)-5α-androstane;

3-oxo-4-aza-4,7β-dimethyl-16β-(4-nitrophenoxy)-5α-androstane;

3-oxo-4-aza-4,7β-dimethyl-16β-(1-naphthyloxy)-5α-androstane;

3-oxo-4-aza-4,7β-dimethyl-16β-(3-chloro-4-methylphenoxy)-5α-androstane;

3-oxo-4-aza-4,7β-dimethyl-16β-(4-methylphenoxy)-5α-androstane;

3-oxo-4-aza-4,7β-dimethyl-16β-(4-trifluoromethylphenoxy)-5α-androstane;

3-oxo-4-aza-4,7β-dimethyl-16β-(4-trifluoromethoxyphenoxy)-5α-androstane;

3-oxo-4-aza-4,7β-dimethyl-16β-(4-methylsulfonylphenoxy)-5α-androstane;

3-oxo-4-aza-4,7β-dimethyl-16β-[4-(4-tolylsulfonylamino)phenoxy]-5α-androstane;

3-oxo-4-aza-4,7β-dimethyl-16β-[(4-phenyl)phenoxy)-5α-androstane;

3-oxo-4-aza-4,7β-dimethyl-16β-(4-fluorophenoxy)-5α-androstane;

3-oxo-4-aza-4,7β-dimethyl-16β-[4-(5-oxazolyl)phenoxy]-5α-androstane;

3-oxo-4-aza-4,7β-dimethyl-16β-[4-(1-pyrryl)phenoxy]-5α-androstane;

3-oxo-4-aza-4,7β-dimethyl-16β-(4-aminophenoxy)-5α-androstane;

3-oxo-4-aza-4,7β-dimethyl-16β-(4-acetylaminophenoxy)-5α-androstane;

3-oxo-4-aza-4,7β-dimethyl-16β-(4-benzoylaminophenoxy)-5α-androstane;

3-oxo-4-aza-4,7β-dimethyl-16β-(4-chlorophenoxy)-5α-androstane;

3-oxo-4-aza-4,7β-dimethyl-16β-(phenoxy)-5α-androstane;

3-oxo-4-aza-4,7β-dimethyl-16β-(2-chlorophenoxy)-5α-androstane;

3-oxo-4-aza-4,7β-dimethyl-16β-(3-chlorophenoxy)-5α-androstane;

and the pharmaceutically acceptable salts thereof.

Particularly useful compounds of structural Formula I are 3-oxo-4-aza-4,7β-dimethyl-16β-(4-chlorophenoxy)-5α-androstane, 3-oxo-4-aza-4,7β-dimethyl- 16β-(phenoxy)-5α-androstane, and 3-oxo-4-aza-7-methyl-16β-(4-methylphenoxy)-5α-androst-1-ene, or pharmaceutically acceptable salts thereof.

As used herein "alkyl" is intended to include both branched-and straight-chain saturated aliphatic hydrocarbon groups having the specified number of carbon atoms, e.g., methyl (Me), ethyl (Et), propyl, butyl, pentyl, hexyl, heptyl, octyl, nonyl, decyl, iso-propyl (i-Pr), iso-butyl (i-Bu), tert-butyl (t-Bu), sec-butyl (s-Bu), iso-pentyl, and the like. "Alkyloxy" (or "alkoxy") represents an alkyl group having the indicated number of carbon atoms attached through an oxygen bridge, e.g., methoxy, ethoxy, propyloxy, and the like. "Alkenyl" is intended to include hydrocarbon groups of either a straight or branched configuration with one or more carbon-carbon double bonds which may occur in any stable point along the chain, such as ethenyl, propenyl or allyl, butenyl, pentenyl, and the like. Included in this invention are all E, Z diastereomers.

The alkyl and alkenyl groups can be unsubstituted or substituted with one or more, and preferably 1–3, of:

i) halo; hydroxy; cyano; nitro; mono-, di- or trihalomethyl; oxo; hydroxysulfonyl; carboxy;

ii) hydroxyC$_{1-6}$ alkyl; C$_{1-6}$ alkyloxy; C$_{1-6}$ alkylthio; C$_{1-6}$ alkylsulfonyl; C$_{1-6}$ alkyloxycarbonyl; in which the C$_{1-6}$ alkyl moiety can be further substituted with 1–3 of: halo; C$_{1-4}$ alkoxy; or trifluoromethyl;

iii) arylthio; aryl; aryloxy; arylsulfonyl; aryloxycarbonyl; in which the aryl moiety can be further substituted with 1–3 of: halo; C$_{1-4}$ alkyl; C$_{1-4}$ alkoxy; or trifluoromethyl;

iv) —C(O)NR$_b$R$_c$; —N(R$_b$)—C(O)—R$_c$; —NR$_b$R$_c$; where R$_b$ and R$_c$ are defined above; and halo is F, Cl, Br or I.

As used herein the term "aryl", i.e., C$_{6-10}$ aryl, is intended to mean phenyl or naphthyl, including 1-naphthyl and 2-naphthyl, either unsubstituted or substituted as described below.

The term "heteroaryl" as used herein, is intended to include a 5, 6 or 7 membered heteroaromatic radical containing at least one member selected from the group consisting of: one ring oxygen atom, one ring sulfur atom, 1–4 ring nitrogen atoms, or combinations thereof; in which the heteroaryl ring can also be fused with one benzo or heteroaromatic ring. This category includes the following either unsubstituted or substituted heteroaromatic rings (as described below): pyridyl, furyl, pyrryl, thienyl, isothiazolyl, imidazolyl, benzimidazolyl, tetrazolyl, pyrazinyl, pyrimidyl, quinolyl, quinazolinyl, isoquinolyl, benzofuryl, isobenzofuryl, benzothienyl, pyrazolyl, indolyl, isoindolyl, purinyl, carbazolyl, isoxazolyl, thiazolyl, isothiazolyl, oxazolyl, benzthiazolyl, and benzoxazolyl. The heteroaryl ring may be attached within structural Formula I by a heteroatom, e.g., N, or carbon atom in the ring, which results in the creation of a stable structure. The heteroaryl ring can also be fused to a benzo ring.

The one to three, and more usefully one to two substituents which can be on the C$_{6-10}$ aryl and heteroaryl groups named above are independently selected from:

v) halo; hydroxy; cyano; nitro; mono-, di- or trihalomethyl; mono-, di- or trihalomethoxy; C$_{2-6}$ alkenyl; C$_{3-6}$ cycloalkyl; formyl; hydrosulfonyl; carboxy; ureido;

vi) C$_{1-6}$ alkyl; hydroxy C$_{1-6}$ alkyl; C$_{1-6}$ alkyloxy; C$_{1-6}$ alkyloxy C$_{1-6}$ alkyl; C$_{1-6}$ alkylcarbonyl; C$_{1-6}$ alkylsulfonyl; C$_{1-6}$ alkylthio; C$_{1-6}$ alkylsulfinyl; C$_{1-6}$ alkylsulfonamido; C$_{1-6}$ alkylarylsulfonamido; C$_{1-6}$ alkyloxycarbonyl; C$_{1-6}$ alkyloxycarbonyl C$_{1-6}$ alkyl; R$_b$R$_c$N—C(O)—C$_{1-6}$ alkyl; C$_{1-6}$ alkanoylamino C$_{1-6}$ alkyl; aroylamino C$_{1-6}$ alkyl; wherein the C$_{1-6}$ alkyl moiety can be substituted with 1–3 of: halo; C$_{1-4}$ alkoxy; or trifluoromethyl;

vii) aryl; aryloxy; arylcarbonyl; arylthio; arylsulfonyl; arylsulfinyl; arylsulfonamido; aryloxycarbonyl; wherein the aryl moiety can be substituted with 1–3 of: halo; C$_{1-4}$ alkyl; C$_{1-4}$ alkoxy; or trifluoromethyl;

viii) —C(O)NR$_b$R$_c$; —O—C(O)—NR$_b$R$_c$; —N(R$_b$)—C(O)—R$_c$; —NR$_b$R$_c$; R$_b$—C(O)—N(R$_c$)—; where R$_b$ and R$_c$ are defined in (e) above; and —N(R$_b$)—C(O)—OR$_c$, wherein this instance R$_c$ is C$_{1-6}$ alkyl or aryl; —N(R$_b$)—C(O)NRCR$_d$, wherein R$_d$ is selected from H, C$_{1-6}$ alkyl, and aryl; in which said C$_{1-6}$ alkyl and aryl can be substituted as described above in (e) for R$_b$ and R$_c$;

ix) a heterocyclic group, which is a 5, 6 or 7 membered ring, containing at least one member selected from the group consisting of: one ring oxygen atom, one ring sulfur atom, 1–4 ring nitrogen atoms, or combinations thereof; in which the heterocyclic ring can be aromatic, unsaturated, or saturated, and wherein the heterocyclic ring can be fused with a benzo ring, and wherein said heterocyclic ring can be substituted with one to three substituents, as defined above for v), vi), vii) and viii), excluding ix) a heterocyclic group.

The fused heteroaromatic ring systems include: purine, imidazoimidazole, imidazothiazole, pyridopyrimidine, pyridopyridazine, pyrimidopyrimidine, imidazopyridazine, pyrrolopyridine, imidazo-pyridine, and the like.

The "heterocyclic" group includes the fully unsaturated heteroaryl rings described above and also their respective dihydro, tetrahydro and hexahydro derivatives resulting in partially unsaturated and fully saturated versions of the ring systems. Examples include: dihydroimidazolyl, dihydrooxazolyl, dihydropyridyl, tetrahydrofuryl, dihydropyrryl, tetrahydrothienyl, dihydroisothiazolyl, 1,2-dihydrobenz-imidazolyl, 1,2-dihydrotetrazolyl, 1,2-dihydropyrazinyl, 1,2-dihydro-pyrimidyl, 1,2-dihydroquinolyl, 1,2,3,4-tetrahydroisoquinolyl, 1,2,3,4-tetrahydrobenzofuryl, 1,2,3,4-tetrahydroisobenzofuryl, 1,2,3,4-tetra-hydrobenzothienyl, 1,2,3,4-tetrahydropyrazolyl, 1,2,3,4-tetrahydro-indolyl, 1,2,3,4-tetrahydroisoindolyl, 1,2,3,4-tetrahydropurinyl, 1,2,3,4-tetrahydrocarbazolyl, 1,2,3,4-tetrahydroisoxazolyl, 1,2,3,4-tetrahydro-thiazolyl, 1,2,3,4-tetrahydrooxazolyl, 1,2,3,4-tetrahydrobenzthiazolyl, and 1,2,3,4-tetrahydrobenzoxazolyl and the like.

The heterocyclic group can be substituted in the same fashion as described above for heteroaryl.

Whenever the terms "alkyl", "alkenyl", "alkyloxy (or alkoxy)", "aryl" or "heteroaryl", or one of their prefix roots, appear in a name of a substituent in Formula I, (e.g., aralkoxyaryloxy) they shall have the same definitions as those described above for "alkyl", "alkenyl", "alkyloxy (or alkoxy)", "aryl" and "heteroaryl", respectively. Designated numbers of carbon atoms (e.g., $C_{1-10}$) shall refer independently to the number of carbon atoms in an alkyl or alkenyl moiety or to the alkyl or alkenyl portion of a larger substituent in which alkyl or alkenyl appears as its prefix root.

The term "pharmaceutically acceptable salt" is intended to include all acceptable salts such as acetate, lactobionate, benzenesulfonate, laurate, benzoate, malate, bicarbonate, maleate, bisulfate, mandelate, bitartrate, mesylate, borate, methylbromide, bromide, methylnitrate, calcium edetate, methylsulfate, camsylate, mucate, carbonate, napsylate, chloride, nitrate, clavulanate, N-methylglucamine, citrate, ammonium salt, dihydrochloride, oleate, edetate, oxalate, edisylate, pamoate (embonate), estolate, palmitate, esylate, pantothenate, fumarate, phosphate/diphosphate, gluceptate, polygalacturonate, gluconate, salicylate, glutamate, stearate, glycollylarsanilate, sulfate, hexylresorcinate, subacetate, hydrabamine, succinate, hydrobromide, tannate, hydrochloride, tartrate, hydroxynaphthoate, teoclate, iodide, tosylate, isothionate, triethiodide, lactate, panoate, valerate, and the like which can be used as a dosage form for modifying the solubility or hydrolysis characteristics or can be used in sustained release or pro-drug formulations.

The subject treated in the methods above is a female mammal, preferably a human being, diagnosed with polycystic ovary syndrome or ovarian or adrenal hyperandrogenism. Alternatively the subject treated is a human mammal, or preferably a human being, who is infertile due to irregular menstrual cycles and/or undergoing treatment with in vitro fertilization due to idiopathic infertility.

The term "therapeutically effective amount" means the amount the compound of structural formula I that will elicit the biological or medical response of a tissue, system, animal or human that is being sought by the researcher, veterinarian, medical doctor or other clinician.

The term "composition" as used herein is intended to encompass a product comprising the specified ingredients in the specified amounts, as well as any product which results, directly or indirectly, from combination of the specified ingredients in the specified amounts.

By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention or a prodrug of a compound of the invention to the individual in need of treatment.

The administration of the compound of structural formula I in order to practice the present methods of therapy is carried out by administering an effective amount of the compound of structural formula I to the patient in need of such treatment or prophylaxis. The need for a prophylactic administration according to the methods of the present invention is determined via the use of well known risk factors. The effective amount of an individual compound is determined, in the final analysis, by the physician in charge of the case, but depends on factors such as the exact disease to be treated, the severity of the disease and other diseases or conditions from which the patient suffers, the chosen route of administration other drugs and treatments which the patient may concomitantly require, and other factors in the physician's judgment.

Generally, the daily dosage of the compound of structural formula I may be varied over a wide range from 0.01 to 1000 mg per adult human per day. Most preferably, dosages range from 0.1 to 100 mg/day. For oral administration, the compositions are preferably provided in the form of tablets.containing 0.01 to 1000 mg, particularly 0.01, 0.05, 0.1, 0.5, 1.0, 2.5, 3.0, 5.0, 6.0, 10.0, 15.0, 25.0, and 50.0 and 100 milligrams of the active ingredient for the symptomatic adjustment of the dosage to the patient to be treated.

The dose may be administered in a single daily dose or the total daily dosage may be administered in divided doses of two, three or four times daily. Furthermore, when administered via intranasal routes, transdermal routes, by rectal suppositories, or through a continual intravenous solution, the dosage administration will, of course, be continuous rather than intermittent throughout the dosage regimen.

Formulations of the 5α-reductase inhibitor employed in the present method for medical use comprise the compound of structural formula I together with an acceptable carrier thereof and optionally other therapeutically active ingredients. The carrier must be pharmaceutically acceptable in the sense of being compatible with the other ingredients of the formulation and not deleterious to the recipient subject of the formulation.

The present invention, therefor further provides a pharmaceutical formulation comprising the compound of structural formula I together with a pharmaceutically acceptable carrier thereof.

The formulations include those suitable for oral, rectal, intravaginal, topical or parenteral (including subcutaneous, intramuscular and intravenous administration). Preferred are those suitable for oral administration.

The formulations may be presented in a unit dosage form and may be prepared by any of the methods known in the art of pharmacy. All methods include the step of bringing the active compound in association with a carrier which constitutes one or more ingredients. In general, the formulations are prepared by uniformly and intimately bringing the active compound in association with a liquid carrier, a waxy solid carrier or a finely divided solid carrier, and then, if needed, shaping the product into desired dosage form.

Formulations of the present invention suitable for oral administration may be presented as discrete units such as capsules, cachets, tablets or lozenges, each containing a predetermined amount of the active compound; as a powder or granules; or a suspension or solution in an aqueous liquid or non-aqueous liquid, e.g., a syrup, an elixir, or an emulsion.

A tablet may be made by compression or molding, optionally with one or more accessory ingredients. Compressed tablets may be prepared by compressing in a suitable machine the active compound in a free flowing form, e.g., a powder or granules, optionally mixed with accessory ingredients, e.g., binders, lubricants, inert diluents, disintegrating agents or coloring agents. Molded tablets may be made by molding in a suitable machine a mixture of the active compound, preferably in powdered form, with a suitable carrier. Suitable binders include, without limitation, starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include, without limitation, sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

Oral liquid forms, such as syrups or suspensions in suitably flavored suspending or dispersing agents such as the synthetic and natural gums, for example, tragacanth, acacia, methyl cellulose and the like may be made by adding the active compound to the solution or suspension. Additional dispersing agents which may be employed include glycerin and the like.

Formulations for vaginal or rectal administration may be presented as a suppository with a conventional carrier, i.e., a base that is nontoxic and nonirritating to mucous membranes, compatible with the compound of structural formula I, and is stable in storage and does not bind or interfere with the release of the compound of structural formula I. Suitable bases include: cocoa butter (theobroma oil), polyethylene glycols (such as carbowax and polyglycols), glycol-surfactant combinations, polyoxyl 40 stearate, polyoxyethylene sorbitan fatty acid esters (such as Tween, Myrj, and Arlacel), glycerinated gelatin, and hydrogenated vegetable oils. When glycerinated gelatin suppositories are used, a preservative such as methylparaben or propylparaben may be employed.

Topical preparations containing the active drug component can be admixed with a variety of carrier materials well known in the art, such as, e.g., alcohols, aloe vera gel, allantoin, glycerine, vitamin A and E oils, mineral oil, PPG2 myristyl propionate, and the like, to form, e.g., alcoholic solutions, topical cleansers, cleansing creams, skin gels, skin lotions, and shampoos in cream or gel formulations. See, e.g., EP 0 285 382.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinyl-pyrrolidone, pyran copolymer, polyhydroxypropylmethacrylamide-phenol, polyhydroxy-ethylaspartamidephenol, or polyethyleneoxide polylysine substituted with palmitoyl residues. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

Formulations suitable for parenteral administration include formulations which comprise a sterile aqueous preparation of the active compound which is preferably isotonic with the blood of the recipient. Such formulations suitably comprise a solution or suspension of a compound that is isotonic with the blood of the recipient subject. Such formulations may contain distilled water, 5% dextrose in distilled water or saline and the active compound. Often it is useful to employ a pharmaceutically and pharmacologically acceptable acid addition salt of the active compound that has appropriate solubility for the solvents employed. Useful salts include the hydrochloride isothionate and methanesulfonate salts. Useful formulations also comprise concentrated solutions or solids comprising the active compound which on dilution with an appropriate solvent give a solution suitable for parenteral administration.

The compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydro-pyrans, polycyanoacrylates and cross-linked or amphipathic block copolymers of hydrogels.

The pharmaceutical composition and method of the present invention may further comprise other therapeutically active compounds usually applied in the treatment of the above mentioned pathological conditions, for instance: GnRH analogues, oral contraceptives, antiandrogens, clomiphene, gonadotropins, or steroids, such as prednisone, estrogens and progestins.

The composition and method of the present invention may further comprise a type 2 $5\alpha$-reductase inhibitor or a dual $5\alpha$-reductase inhibitor. Preferred type 2 $5\alpha$-reductase inhibitors for use in the present composition and method include: finasteride and epristeride. A preferred dual inhibitor is: $17\beta$-N-(2,5-bis(trifluoromethyl))phenyl carbamoyl-4-aza-$5\alpha$-androst-1-en-3-one.

One aspect of the present invention provides a method for treating polycystic ovary syndrome comprising administering to a female mammal in need of treatment an effective amount of a compound of structural formula I.

Another aspect of the present invention provides a method of improving fertility and the response to in vitro fertilization (I.V.F.) comprising administering to a female mammal in need of treatment and effective amount of a compound of structural formula I.

In particular, when a type 2 $5\alpha$-reductase inhibitor or a dual $5\alpha$-reductase inhibitor is employed, dosages of 0.01 to 10 mg per adult human per day are appropriate for treatment, more preferably 1 to 5 mg/day especially preferred is about 5 mg/day.

The compounds of the methods of the present invention can be administered by a variety of routes including oral, rectal, vaginal, transdermal, subcutaneous, intravenous, intramuscular, and intranasal, and such compounds are preferably formulated prior to administration. Therefore, another embodiment of the present invention is a pharmaceutical formulation comprising an effective amount of a compound of structural formula I or a pharmaceutically acceptable salt thereof, a dual 5α-reductase inhibitor, and a pharmaceutically acceptable carrier, diluent or excipient therefor.

In accordance with the method of the present invention, the individual components of the combination can be administered separately at different times during the course of therapy or concurrently in divided or single combination forms. The instant invention is therefore to be understood as embracing all such regimes of simultaneous or alternating treatment and the term "administering" is to be interpreted accordingly. It will be understood that the scope of combinations of the compounds of this invention with other agents useful for treating polycystic ovary syndrome and with other agents useful in improving fertility and the response to in vitro fertilization (I.V.F.) by employing a 5α-reductase type 1 inhibitor.

The compounds of structural formula I may be prepared as described in PCT publication WO 95/11254, and are available to one of ordinary skill in the art.

The 5α-reductase type 2 inhibitor finasteride that may employed this invention can be prepared as described in U.S. Pat. No. 4,760,071.

The following examples are not intended to be limitations on the scope of the instant invention in any way, and they should not be so construed. Furthermore, examples are not to be construed as forming the only methods and compositions that are considered as the invention. Those skilled in the art will readily understand that known variations of the conditions, processes, methods and compositions of the following preparative procedures can be used.

EXAMPLE 1

Distribution of 5α-reductase in Pregnant Rat Tissues

Enzyme Preparation:

Rat ovary was obtained from pregnant animals (gestational days 15, 17, 19, 20, 21 and 22 and was pulverized using a freezer mill and homogenized in 20 mM potassium phosphate pH 6.5, 5 mM magnesium sulfate, 25 mM potassium chloride, 1 mM phenylmethylsulfonyl fluoride, 1 mM DTT, 5 μM NADPH, and 0.25 M sucrose using a dounce homogenizer. Glycerol was added to the homogenate to a final concentration of 20%.

Enzyme Assay:

The reaction mixture contained 33 mM succinic acid 44 mM imidazole, 33 mM diethanolamine (SID), pH 5.5 or pH 7.0, 0.3–15 μM [7-$^3$H]-testosterone (T) (specific activity approximately 20–30 Ci/mmol) or [1,2-$^3$H]-progesterone, 1 mM DTT and 0.5 mM NADPH in a final volume of 0.1 mL. The assay was initiated by the addition of enzyme and incubated at 37° C. for 20–30 minutes. The reaction was quenched with cyclohexane:ethyl acetate (70:30 v/v) and product peaks were separated by normal phase HPLC. Alternatively, samples were also quenched using 0.05 M phosphoric acid in 10% ethanol. The product profile was analyzed by reverse phase HPLC.

Product Assignments

Products produced in the enzymatic assays were assigned based on mobility on normal or reverse phase HPLC compared to authentic standards. The normal phase HPLC system consisted of a 25 cm Whatman Partisil 5 silica column equilibrated in cyclohexane:ethyl acetate (65:35) at 1 mL/min. Under these conditions, retention times were as follows: dihydrotestosterone (DHT), 7 min; androstenedione, 8 min; 3α/β-androstane diol, 9.5 min; testosterone (T), 11 min. For assays using progesterone (P) as substrate, the conditions were modified to cyclohexane:ethyl acetate (78:22) at 1.5 mL/min. Under these conditions, retention times for authentic steroids were as follows: progesterone 9.8 min; 3 α/3β-androstane diol, 8 min; 20α-hydroxyprogesterone, 17 min. Variations ±3.5 min in retention times for the products were seen, but similar shifts were observed in the retention times of standards. The absolute assignment of 3α- versus 3β-androstanediol was made on the basis of mobility on reverse phase HPLC. The sample was chromatographed on a 25 cm Whatman Partisil 5 ODS-3 column that was equilibrated in methanol:water:acetonitrile (3:3:1) at 1.5 mL/min. Under these conditions, authentic steroids had retention times of 37 min and 24 min for 3α- and 3β-androstanediol, respectively.

Results:

Metabolism of testosterone: Homogenates of rat ovary from pregnant animals were incubated with 0.3 μM $^3$H-testosterone (T) or $^3$H-progesterone (P) and the products analyzed by HPLC. Product assignments were based on comparison of retention times of unknowns to those of authentic standards on normal phase HPLC. Table 1, below shows representative examples of product distribution using T as substrate.

TABLE 1

Metabolism of T by pregnant rat ovary at gestation day 19

| | | % product | | | | |
|---|---|---|---|---|---|---|
| retention time, min | | 6.9 DHT | 7.8 A | 9.3 Adiol | 10.7 T | 13.6 unknown |
| ovary | 640 μg | 0.22 | 1.3 | 0.83 | 96 | 2.1 |

Three products were observed which migrated at ~6.9 min, ~7.8 min and ~9.3 min. These products were identified as DHT, A (androstenedione) and 3-androstane diol (Adiol). Although 3α- and 3β-androstane diol co-migrate by normal phase HPLC, these two steroids are readily separated by reverse phase HPLC. Using this methodology, the product from the enzymatic reaction was defined as 3α-androstane diol. Two non-5α-reduced products were also detected: androstenediol (~7.8 min), the product of 17β-hydroxysteroid dehydrogenase, and an unidentified metabolite (~13.6 min). The unidentified metabolite most likely represents a ring hydroxylation product.

Metabolism of progesterone: A representative product profile when P is used as substrate is presented in Table 2 and for the most part mirrors the pattern of products seen with T.

TABLE 2

Metabolism of P by pregnant rat ovary at gestation day 19

| | | % product | | | | |
|---|---|---|---|---|---|---|
| retention time, min | | 5.5 DHP | 8.3 3α-hydP | 9.5 P | 12.2 unknown | 17.6 20α-hydP |
| ovary | 286 μg | 0.22 | 1.3 | 0.83 | 96 | 2.1 |

3α-hydP - 3α-hydroxy-5α-pregnan-20-one
20α-hydP - 20α-hydroxyprogesterone

Progesterone undergoes 5α-reduction to dihydroprogesterone (DHP) and subsequent reduction of DHP by 3a-hydroxysteroid dehydrogenase to 3α-hydroxy-5α-pregnan-20-one. The unknown product at 12.1 minutes most likely represents-the same proposed ring hydroxylation step discussed for testosterone metabolism. One obvious difference in P metabolism is conversion to 20α-hydroxyP (~17.6 min) by 20α-hydroxysteroid dehydrogenase. P is not a substrate for 17β-hydroxysteroid dehydrogenase and therefore no product is expected for this enzyme.

Specific activity/Isozyme determination: The specific activity of the enzyme was determined using T as substrate. The combined contribution of DHT and androstanediol was used for this analysis. As shown in Table 3, there is very little change in the 5α-reductase content of the tissues from gestation day 15 to 22.

TABLE 3

Steroid 5α-reductase specific activity determination in pregnant rat ovary[1]

| animal | gestation day | pmol/min/mg |
|---|---|---|
| 4701 | 15 | 0.8 |
| 4700 | 15 | 2.9 |
| 4703 | 17 | 1.4 |
| 4705 | 19 | 1.3 |
| 4704 | 19 | 0.7 |
| 4707 | 20 | 2.0 |
| 4706 | 20 | 1.5 |
| 4708 | 21 | 1.4 |
| 4711 | 22 | 1.4 |
| 4710 | 22 | 1.8 |
| average | | 1.5 ± 1.6 |

[1]assay conducted with 15 µM T

An initial attempt was made to define the isozyme content of the tissues by comparing the 5α-reductase activity at pH 5.5 and 7.0. Under these assay conditions, the ratio of activity at the two pH's can predict isozyme content. This assessment is based on the difference in pH optimum of 7.0 and 5.5 for the type 1 and type 2 5α-reductases, respectively. The results of these studies are presented in Table 4.

TABLE 4

Isozyme content of rat ovary obtained on gestation day 21 as determined by pH/activity analysis

| % conversion | | specific act. | ratio | Predominant |
|---|---|---|---|---|
| pH 5.5 | pH 7.0 | pmol/min/mg | pH 5.5/7.0 | Isozyme |
| 1.2 | 2 | 1.5 | 1.2 | 1 |

A ratio of 1 or lower suggests that the predominant enzyme is type 1, while a higher ratio indicates that the predominant enzyme is type 2. This study suggests that type 1 5α-reductase is present in ovary.

EXAMPLE 2

Oral Composition

As a specific embodiment of an oral composition of a compound of this invention, 3 mg of 3-oxo-4-aza-4,7β-dimethyl-16β-(phenoxy)-5α-androstane is formulated with sufficient finely divided lactose to provide a total amount of 580 to 590 mg to fill a size 0 hard gelatin capsule.

EXAMPLE 3

Oral Composition

As a specific embodiment of an oral composition of a compound of this invention, 0.5 mg of 3-oxo-4-aza-7-methyl-16β-(4-methylphenoxy)-5α-androst-1-ene is formulated with sufficient finely divided lactose to provide a total amount of 580 to 590 mg to fill a size 0 hard gelatin capsule.

EXAMPLE 4

Oral Composition

As a specific embodiment of an oral composition of a compound of this invention, 2.5 mg of a compound of structural formula I is formulated with sufficient finely divided lactose to provide a total amount of 580 to 590 mg to fill a size 0 hard gelatin capsule.

EXAMPLE 5

Oral Composition

As a specific embodiment of an oral composition of a compound of this invention, 6 mg of 3-oxo-4-aza-4,7β-dimethyl-16β-(4-chlorophenoxy)-5α-androstane is formulated with sufficient finely divided lactose to provide a total amount of 580 to 590 mg to fill a size 0 hard gelatin capsule.

EXAMPLE 6

| Transdermal Patch Formulation | |
|---|---|
| Ingredient | Amount |
| 3-oxo-4-aza,4,7β-dimethyl-16β-(phenoxy)-5α-androstane | 40 g |
| Silicone fluid | 45 g |
| Colloidal silicone dioxide | 2.5 g |

The silicone fluid and 3-oxo-4-aza-4,7β-dimethyl-16β-(phenoxy)-5α-androstane are mixed together and the colloidal silicone dioxide is added to increase viscosity. The material is then dosed into a subsequently heat sealed polymeric laminate comprised of the following: polyester release liner, skin contact adhesive composed of silicone or acrylic polymers, a control membrane which is a polyolefin (e.g. polyethylene, polyvinyl acetate or polyurethane), and an impermeable backing membrane made of a polyester multilaminate. The resulting laminated sheet is then cut into 10 cm$^2$ patches. For 100 Patches.

EXAMPLE 7

| Suppository | |
|---|---|
| Ingredient | Amount |
| 3-oxo-4-aza-7-methyl-16β-(4-methylphenoxy)-5α-androst-1-ene | 25 g |
| Polyethylene glycol 1000 | 1481 g |
| Polyethylene glycol 4000 | 494 g |

The polyethylene glycol 1000 and polyethylene glycol 4000 are mixed and melted. The 3-oxo-4-aza-7-methyl-16β-(4-methylphenoxy)-5α-androst-1-ene is mixed into the molten mixture, poured into molds and allowed to cool. For 1000 suppositories.

EXAMPLE 8

| Injectable solution | |
|---|---|
| Ingredient | Amount |
| compound of structural formula I | 5 g |
| Buffering agents | q.s. |

-continued

| Injectable solution | |
|---|---|
| Ingredient | Amount |
| Propylene glycol | 400 mg |
| Water for injection | 600 mL |

The compound of structural formula I and buffering agents are dissolved in the propylene glycol at about 50° C. The water for injection is then added with stirring and the resulting solution is filtered, filled into ampules, sealed and sterilized by autoclaving. For 1000 Ampules.

EXAMPLE 9

| Injectable solution | |
|---|---|
| Ingredient | Amount |
| 3-oxo-4-aza-4,7β dimethyl-16β-(4-chlorophenoxy)-5α-androstane | 5 g |
| Buffering agents | q.s. |
| Magnesium sulfate heptahydrate | 100 mg |
| Water for injection | 880 mL |

The 3-oxo-4-aza-4,7β-dimethyl-16β-(4-chlorophenoxy)-5α-androstane, magnesium sulfate heptahydrate and buffering agents are dissolved in the water for injection with stirring, and the resulting solution is filtered, filled into ampules, sealed and sterilized by autoclaving. For 1000 Ampules.

EXAMPLE 10

Oral Composition

As a specific embodiment of an oral composition of a compound of this invention, 5 mg of 3-oxo-4-aza-4,7β-dimethyl-16β-(phenoxy)-5α-androstane, and 3 mg of finasteride (17β-(N-tert-butylcarbamoyl)-3-oxo-4-aza-5α-androst-1-en-3-one) are formulated with sufficient finely divided lactose to provide a total amount of 580 to 590 mg to fill a size 0 hard gelatin capsule.

EXAMPLE 11

Preparation of Human Prostatic and Scalp 5α-Reductases

Samples of human tissue were pulverized using a freezer mill and homogenized in 40 mM potassium phosphate, pH 6.5, 5 mM magnesium sulfate, 25 mM potassium chloride, 1 mM phenylmethyl-sulfonyl fluoride, 1 mM dithiothreitol (DTT) containing 0.25 M sucrose using a Potter-Elvehjem homogenizer. A crude nuclear pellet was prepared by centrifugation of the homogenate at 1,500×g for 15 min. The crude nuclear pellet was washed two times and resuspended in two volumes of buffer. Glycerol was added to the resuspended pellet to a final concentration of 20%. The enzyme suspension was frozen in aliquots at −80° C. The prostatic and scalp reductases were stable for at least 4 months when stored under these conditions.

EXAMPLE 12

5α-Reductase Assay

Not applicable.

The reaction mixture for the type 1 5α-reductase contained 40 mM potassium phosphate, pH 6.5, 5 mM [7-$^3$H]-testosterone, 1 mM dithiothreitol and 500 μM NADPH in a final volume of 100 μL. The reaction mixture for the type 2 5β-reductase contained 40 mM sodium citrate, pH 5.5, 0.3 mM [7-$^3$H]-testosterone, 1 mM dithiothreitol and 500 μM NADPH in a final volume of 100 μL. Typically, the assay was initiated by the addition of 50–100 μg prostatic homogenate or 75–200 μg scalp homogenate and incubated at 37° C. After 10–50 min the reaction was quenched by extraction with 250 μL of a mixture of 70% cyclohexane: 30% ethyl acetate containing 10 μg each DHT and T. The aqueous and organic layers were separated by centrifugation at 14,000 rpm in an Eppendorf microfuge. The organic layer was subjected to normal phase HPLC (10 cm Whatman Partisil 5 silica column equilibrated in 1 ml/min 70% cyclohexane: 30% ethyl acetate; retention times: DHT, 6.8–7.2 min; androstanediol, 7.6–8.0 min; T, 9.1–9.7 min). The HPLC system consisted of a Waters Model 680 Gradient System equipped with a Hitachi Model 655α Autosampler, Applied Biosystems Model 757 variable UV detector, and a Radiomatic Model A120 radioactivity analyzer. The conversion of T to DHT was monitored using the radioactivity flow detector by mixing the HPLC effluent with one volume of Flo Scint 1 (Radiomatic). Under the conditions described, the production of DHT was linear for at least 25 min. The only steroids observed with the human prostate and scalp preparations were T, DHT and androstanediol.

Inhibition Studies

Compounds were dissolved in 100% ethanol. The compound to be tested was pre-incubated with the enzyme (either 5α-reductase type 1 or 2) prior to initiation by addition of substrate testosterone. $IC_{50}$ values represent the concentration of inhibitor required to decrease enzyme conversion of testosterone to dihydrotestosterone by 50% of the control. $IC_{50}$ values were determined using a 6 point titration where the concentration of the inhibitor was varied from 0.1 to 1000 nM. Representative compounds of this invention were tested in the above described assay for 5α-reductase type 1 and type 2 inhibition.

A compound referred to herein as a 5α-reductase 2 inhibitor is a compound that shows inhibition of the 5α-reductase 2 isozyme in the above-described assay, having an $IC_{50}$ value of about or under 100 nM.

The compounds are tested in the above-described assay for 5α-reductase type 1 and type 2 inhibition, and were found to have $IC_{50}$ values under about 100 nM for inhibition of the type 1 isozyme. Compounds found to have $IC_{50}$ values of under about 50 nM for inhibition of the type 1 isozyme are called type 1 inhibitors. Compounds called "dual inhibitors" additionally had $IC_{50}$'s under about 200 nM for inhibition of the type 2 isozyme.

While the invention has been described and illustrated with reference to certain particular embodiments thereof, those skilled in the art will appreciate that various changes, modifications and substitutions can be made therein without departing from the spirit and scope of the invention. For example, effective dosages other than the particular dosages as set forth herein above may be applicable as a consequence of variations in the responsiveness of the mammal being treated for any of the indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A method of improving the response to in vitro fertilization which comprises the administration to a subject in need thereof of an effective amount of a compound of structural formula I:

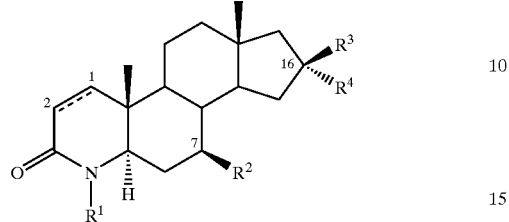

or a pharmaceutically acceptable salt or ester thereof wherein:

the C1–C2 carbon-carbon bond may be a single bond, or a double bond as indicated by the dashed line;

$R^1$ is selected from the group consisting of hydrogen and $C_{1-10}$ alkyl;

$R^2$ is selected from the group consisting of hydrogen and $C_{1-10}$ alkyl;

one of $R^3$ and $R^4$ is selected from the group consisting of hydrogen and methyl, and the other is selected from the group consisting of:
(a) amino;
(b) cyano;
(c) fluoro;
(d) methyl;
(e) OH;
(f) —C(O)$NR_bR_c$, where $R_b$ and $R_c$ are independently H, $C_{1-6}$alkyl, aryl, or aryl$C_{1-6}$alkyl; wherein the alkyl moiety is unsubstituted or substituted with 1 to 3 of: halo; $C_{1-4}$alkoxy; or trifluoromethyl; and the aryl moiety is unsubstituted or substituted with 1 to 3 of: halo; $C_{1-4}$alkyl; $C_{1-4}$alkoxy; or trifluoromethyl;
(g) $C_{1-10}$alkyl-X—;
(h) $C_{2-10}$alkenyl-X—;
wherein the $C_{1-10}$ alkyl in (g) and $C_{2-10}$ alkenyl in (h) can be unsubstituted or substituted with one to three of:
i) halo; hydroxy; cyano; nitro; mono-, di- or trihalomethyl; oxo; hydroxysulfonyl; carboxy;
ii) hydroxy$C_{1-6}$alkyl; $C_{1-6}$alkyloxy; $C_{1-6}$ alkylthio; $C_{1-6}$alkylsulfonyl; $C_{1-6}$ alkyloxycarbonyl; in which the $C_{1-6}$ alkyl moiety is unsubstituted or substituted with 1 to 3 of: halo; $C_{1-4}$ alkoxy; or trifluoromethyl;
iii) arylthio; aryl; aryloxy; arylsulfonyl; aryloxycarbonyl; in which the aryl moiety is unsubstituted or substituted with 1 to 3 of: halo; $C_{1-4}$ alkyl; $C_{1-4}$ alkoxy; or trifluoromethyl;
iv) —C(O)$NR_bR_c$; —N($R_b$)—C(O)—$R_c$; —$NR_bR_c$; where $R_b$ and $R_c$ are defined above;
(i) aryl-X—;
(j) heteroaryl-X—, wherein heteroaryl is a 5, 6 or 7 membered heteroaromatic ring containing at least one member selected from the group consisting of: one ring oxygen atom, one ring sulfur atom, 1–4 ring nitrogen atoms, or combinations thereof; in which the heteroaromatic ring can also be fused with one benzo or heteroaromatic ring; wherein the aryl in (i) and heteroaryl in (j) is unsubstituted or substituted with one to three of:

v) halo; hydroxy; cyano; nitro; mono-, di- or trihalomethyl; mono-, di- or trihalomethoxy; $C_{2-6}$ alkenyl; $C_{3-6}$ cycloalkyl; formyl; hydrosulfonyl; carboxy; ureido;

vi) $C_{1-6}$ alkyl; hydroxy $C_{1-6}$ alkyl; $C_{1-6}$ alkyloxy; $C_{1-6}$ alkyloxy $C_{1-6}$alkyl; $C_{1-6}$ alkylcarbonyl; $C_{1-6}$ alkylsulfonyl; $C_{1-6}$ alkylthio; $C_{1-6}$ alkylsulfinyl; $C_{1-6}$ alkylsulfonamido; $C_{1-6}$ alkylarylsulfonamido; $C_{1-6}$ alkyloxy-carbonyl; $C_{1-6}$ alkyloxycarbonyl $C_{1-6}$alkyl; $R_bR_cN$—C(O)—$C_{1-6}$alkyl; $C_{1-6}$ alkanoylamino $C_{1-6}$ alkyl; aroylamino $C_{1-6}$ alkyl; wherein the $C_{1-6}$ alkyl moiety is unsubstituted or substituted with 1 to 3 of: halo; $C_{1-4}$alkoxy; or trifluoromethyl;

vii) aryl; aryloxy; arylcarbonyl; arylthio; arylsulfonyl; arylsulfinyl; arylsulfonamido; aryloxycarbonyl; wherein the aryl moiety is unsubstituted or substituted with 1 to 3 of: halo; $C_{1-4}$alkyl; $C_{1-4}$alkoxy; or trifluoromethyl;

viii) —C(O)$NR_bR_c$; —O—C(O)—$NR_bR_c$; —N($R_b$)—C(O)—$R_c$; —$NR_bR_c$; $R_b$—C(O)—N($R_c$)—; where $R_b$ and $R_c$ are defined in (f) above; and —N($R_b$)—C(O)—$OR_g$, wherein $R_g$ is $C_{1-6}$alkyl or aryl, in which the alkyl moiety is unsubstituted or substituted with 1 to 3 of: halo; $C_{1-4}$alkoxy; or trifluoromethyl, and the aryl moiety is unsubstituted or substituted with 1 to 3 of: halo; $C_{1-4}$alkyl; $C_{1-4}$ alkoxy, or trifluoromethyl; —N($R_b$)—C(O)$NR_cR_d$, wherein $R_d$ is selected from H, $C_{1-6}$ alkyl, and aryl; in which said $C_{1-6}$alkyl and aryl is unsubstituted or substituted as described above in (f) for $R_b$ and $R_c$;

ix) a heterocyclic group, which is a 5, 6 or 7 membered ring, containing at least one member selected from the group consisting of: one ring oxygen atom, one ring sulfur atom, 1–4 ring nitrogen atoms, or combinations thereof; in which the heterocyclic ring can be aromatic, unsaturated, or saturated, wherein the heterocyclic ring can be fused with a benzo ring, and wherein said heterocyclic ring is unsubstituted or substituted with 1 to 3 substituents, as defined above for v), vi), vii) and viii), excluding ix) a heterocyclic group; and (k) $R^3$ and $R^4$ taken together can be carbonyl oxygen;
(l) $R^3$ and $R^4$ taken together can be =CH—$R_g$, wherein $R_g$ is defined in viii); and wherein:

X is selected from the group consisting of:
—O—; —S(O)$_n$—; —C(O)—; —CH($R_e$)—; —C(O)—O—*; —C(O)—N($R_e$)—*; —N($R_e$)—C(O)—O—*; —O—C(O)—N($R_e$)—*; —N($R_e$)C(O)—N($R_e$)—; —O—CH($R_e$)—*; —N($R_e$)—; wherein $R_e$ is H, $C_{1-3}$ alkyl, aryl, aryl-$C_{1-3}$ alkyl, or unsubstituted or substituted heteroaryl, as defined above in (j);

wherein the asterisk (*) denotes the bond which is attached to the 16-position in Structure I; and n is zero, 1 or 2, or a pharmaceutically acceptable salt thereof.

2. The method of claim 1, wherein the compound of structural formula I is selected from:
4-aza-4,7β-dimethyl-5α-androstane-3,16-dione;
4-aza-4-methyl-5α-androstan-3,16-dione;
3-oxo-4-aza-4-methyl-16β-hydroxy-5α-androstane;
3-oxo-4-aza-4-methyl-16β-(benzylaminocarbonyloxy)-5α-androstane;
3-oxo-4-aza-4-methyl-16β-benzoylamino-5α-androstane;

3-oxo-4-aza-4-methyl-16β-methoxy-5α-androstane;
3-oxo-4-aza-4-methyl-16β-allyloxy-5α-androstane;
3-oxo-4-aza-4-methyl-16β-(n-propyloxy)-5α-androstane;
3-oxo-4-aza-4-methyl-16β-hydroxy-5α-androstane;
3-oxo-4-aza-4-methyl-16β-(phenoxy)-5α-androstane;
3-oxo-4-aza-7β-methyl-16β-(phenoxy)-5α-androst-1-ene;
3-oxo-4-aza-4-methyl-16α-methoxy-5α-androstane;
3-oxo-4-aza-4-methyl-16β-(4-chlorophenoxy)-5α-androstane;
3-oxo-4-aza-7β-methyl-16β-(4-chlorophenoxy)-5α-androst-1-ene;
3-oxo-4-aza-7β-methyl-16β-(4-chlorophenoxy)-5α-androstane;
3-oxo-4-aza-7β-methyl-16β-(3-chloro-4-methylphenoxy)-5α-androstane;
3-oxo-4-aza-7β-methyl-16β-(4-methylphenoxy)-5α-androstane;
3-oxo-4-aza-7β-methyl-16β-(4-methylphenoxy)-5α-androst-1-ene;
3-oxo-4-aza-7β-methyl-16β-[4-(1-pyrrolyl)phenoxy]-5α-androst-1-ene;
3-oxo-4-aza-4,7β-dimethyl-16α-hydroxy-5β-androstane;
3-oxo-4-aza-4,7β-dimethyl-16β-methoxy-5α-androstane;
3-oxo-4-aza-4,7β-dimethyl-16β-allyloxy-5α-androstane;
3-oxo-4-aza-4,7β-dimethyl-16β-(3,3-dimethylallyloxy)-5α-androstane;
3-oxo-4-aza-4,7β-dimethyl-16β-(n-propyloxy)-5α-androstane;
3-oxo-4-aza-4,7β-dimethyl-16β-(iso-pentoxy)-5α-androstane;
3-oxo-4-aza-4,16α-dimethyl-16β-hydroxy-5α-androstane;
3-oxo-4-aza-4,7β-dimethyl-16β-ethyloxy-5α-androstane;
3-oxo-4-aza-4,7β-dimethyl-16β-benzyloxy-5α-androstane;
3-oxo-4-aza-4,7β-dimethyl-16α-hydroxy-5α-androstane;
3-oxo-4-aza-4,7β-dimethyl-16β-methylthio-5α-androstane;
3-oxo-4-aza-4,7β-dimethyl-16β-(n-propylthio)-5α-androstane;
3-oxo-4-aza-4,7β-dimethyl-16β-fluoro-5α-androstane;
3-oxo-4-aza-4,7β-dimethyl-16β-cyano-5α-androstane;
3-oxo-4-aza-4-methyl-16β-(1-hexyl)-5α-androstane;
3-oxo-4-aza-4,7β-dimethyl-16β-(n-propyl)-5α-androstane;
3-oxo-4-aza-4,7β-dimethyl-16β-benzyl-5α-androstane;
3-oxo-4-aza-4,7β-dimethyl-16β-(4-chlorobenzyl)-5α-androstane;
3-oxo-4-aza-4,16α-dimethyl-16β-methoxy-5α-androstane;
3-oxo-4-aza-4,7β-dimethyl-16β-(4-cyanophenoxy)-5α-androstane;
3-oxo-4-aza-4,7β-dimethyl-16β-(3-cyanophenoxy)-5α-androstane;
3-oxo-4-aza-4,7β-dimethyl-16β-(4-nitrophenoxy)-5α-androstane;
3-oxo-4-aza-4,7β-dimethyl-16β-(1-naphthyloxy)-5α-androstane;
3-oxo-4-aza-4,7β-dimethyl-16β-(3-chloro-4-methylphenoxy)-5α-androstane;
3-oxo-4-aza-4,7β-dimethyl-16β-(4-methylphenoxy)-5α-androstane;
3-oxo-4-aza-4,7β-dimethyl-16β-(tert-butyloxy)-5α-androstane;
3-oxo-4-aza-4,7β-dimethyl-16β-(3-methyl-1-butyloxy)-5α-androstane;
3-oxo-4-aza-4,7β-dimethyl-16α-(n-propyloxy)-5α-androstane;
3-oxo-4-aza-4,7β-dimethyl-16β-(4-trifluoromethylphenoxy)-5α-androstane;
3-oxo-4-aza-4,7β-dimethyl-16β-(4-trifluoromethoxyphenoxy)-5α-androstane;
3-oxo-4-aza-4,7β-dimethyl-16β-ethylthio-5α-androstane;
3-oxo-4-aza-4,7β-dimethyl-16β-ethylsulfonyl-5α-androstane;
3-oxo-4-aza-4,7β-dimethyl-16β-(4-methylsulfonylphenoxy)-5α-androstane;
3-oxo-4-aza-4,7β-dimethyl-16β-[4-(4-tolylsulfonylamino)phenoxy]-5α-androstane;
3-oxo-4-aza-4,7β-dimethyl-16β-(3-pyridyloxy)-5α-androstane;
3-oxo-4-aza-4,7β-dimethyl-16β-[(4-phenyl)phenoxy)-5α-androstane;
3-oxo-4-aza-4,7β-dimethyl-16β-(4-fluorophenoxy)-5α-androstane;
3-oxo-4-aza-4,7β-dimethyl-16β-(2-pyrazinyloxy)-5α-androstane;
3-oxo-4-aza-4,7β-dimethyl-16β-[4-(5-oxazolyl)phenoxy]-5α-androstane;
3-oxo-4-aza-4,7β-dimethyl-16β-(2-pyrimidinyloxy)-5α-androstane;
3-oxo-4-aza-4,7β-dimethyl-16β-[4-(1-pyrryl)phenoxy]-5α-androstane;
3-oxo-4-aza-4,7β-dimethyl-16β-(4-aminophenoxy)-5α-androstane;
3-oxo-4-aza-4,7β-dimethyl-16β-(4-acetylaminophenoxy)-5α-androstane;
3-oxo-4-aza-4,7β-dimethyl-16β-(4-benzoylaminophenoxy)-5α-androstane;
3-oxo-4-aza-4,7β-dimethyl-16β-(4-chlorophenoxy)-5α-androstane;
3-oxo-4-aza-4,7β-dimethyl-16β-(phenoxy)-5α-androstane;
3-oxo-4-aza-4,7β-dimethyl-16β-(2-chlorophenoxy)-5α-androstane;
3-oxo-4-aza-4,7β-dimethyl-16β-(3-chlorophenoxy)-5α-androstane;
3-oxo-4-aza-4,7β-dimethyl-16β-(4-chlorophenoxy)-5α-androst-1-ene;
3-oxo-4-aza-4,7β-dimethyl-16-(4-chlorobenzylidene)-5α-androstane;
3-oxo-4-aza-4,7β-dimethyl-16-benzylidene-5α-androstane;
3-oxo-4-aza-4,7β-dimethyl-16-(4-methylbenzylidene)-5α-androstane;
3-oxo-4-aza-4,7β-dimethyl-16-(4-chlorobenzyl)-5α-androstane;
3-oxo-4-aza-4,7β-dimethyl-16-(4-methylbenzyl)-5α-androstane;
3-oxo-4-aza-4,7β-dimethyl-16-(3-pyridylmethyl)-5α-androstane;

3-oxo-4-aza-4,7β-dimethyl-16α-methanesulfonyl-5α-androstane;

3-oxo-4-aza-4,7β-dimethyl-16β-thiophenoxy-5α-androstane;

3-oxo-4-aza-4,7β-dimethyl-16β-(4-chlorothiophenoxy)-5α-androstane;

3-oxo-4-aza-4,7β-dimethyl-16β-(4-fluorothiophenoxy)-5α-androstane;

3-oxo-4-aza-4,7β-dimethyl-16β-(4-methylthiophenoxy)-5α-androstane;

3-oxo-4-aza-4,7β-dimethyl-16β-(4-methoxythiophenoxy)-5α-androstane;

3-oxo-4-aza-4,7β-dimethyl-16β-phenylsulfinyl-5α-androstane;

3-oxo-4-aza-4,7β-dimethyl-16β-phenylsulfonyl-5α-androstane;

3-oxo-4-aza-4,7β,16α-trimethyl-16β-(4-trifluoromethylphenoxy)-5α-androstane;

3-oxo-4-aza-4,7β,16α-trimethyl-16β-hydroxy-5α-androstane;

3-oxo-4-aza-4,7β,16α-trimethyl-16β-methoxy-5α-androstane;

3-oxo-4-aza-4,7β-dimethyl-16β-(4-cyanophenoxy)-5α-androstane;

3-oxo-4-aza-4,7β-dimethyl-16β-(3-cyanophenoxy)-5α-androstane;

3-oxo-4-aza-4,7β-dimethyl-16β-(4-nitrophenoxy)-5α-androstane;

3-oxo-4-aza-4,7β-dimethyl-16β-(1-naphthyloxy)-5α-androstane;

3-oxo-4-aza-4,7β-dimethyl-16β-(3-chloro-4-methylphenoxy)-5α-androstane;

3-oxo-4-aza-4,7β-dimethyl-16β-(4-methylphenoxy)-5α-androstane;

3-oxo-4-aza-4,7β-dimethyl-16β-(4-trifluoromethylphenoxy)-5α-androstane;

3-oxo-4-aza-4,7β-dimethyl-16β-(4-trifluoromethoxyphenoxy)-5α-androstane;

3-oxo-4-aza-4,7β-dimethyl-16β-(4-methylsulfonylphenoxy)-5α-androstane;

3-oxo-4-aza-4,7β-dimethyl-16β-[4-(4-tolylsulfonylamino)phenoxy]-5α-androstane;

3-oxo-4-aza-4,7β-dimethyl-16β-[(4-phenyl)phenoxy)-5α-androstane;

3-oxo-4-aza-4,7β-dimethyl-16β-(4-fluorophenoxy)-5α-androstane;

3-oxo-4-aza-4,7β-dimethyl-16β-[4-(5-oxazolyl)phenoxy]-5α-androstane;

3-oxo-4-aza-4,7β-dimethyl-16β-[4-(1-pyrryl)phenoxy]-5α-androstane;

3-oxo-4-aza-4,7β-dimethyl-16β-(4-aminophenoxy)-5α-androstane;

3-oxo-4-aza-4,7β-dimethyl-16β-(4-acetylaminophenoxy)-5α-androstane;

3-oxo-4-aza-4,7β-dimethyl-16β-(4-benzoylaminophenoxy)-5α-androstane;

3-oxo-4-aza-4,7β-dimethyl-16β-(4-chlorophenoxy)-5α-androstane;

3-oxo-4-aza-4,7β-dimethyl-16β-(phenoxy)-5α-androstane;

3-oxo-4-aza-4,7β-dimethyl-16β-(2-chlorophenoxy)-5α-androstane;

3-oxo-4-aza-4,7β-dimethyl-16β-(3-chlorophenoxy)-5α-androstane;

and the pharmaceutically acceptable salts thereof.

3. The method of claim 1 wherein the compound of structural formula I is selected from:

(a) 3-oxo-4-aza-4,7β-dimethyl-16β-(4-chlorophenoxy)-5α-androstane, (b) 3-oxo-4-aza-4,7β-dimethyl-16β-(phenoxy)-5α-androstane, and (c) 3-oxo-4-aza-7β-methyl-16β-(4-methylphenoxy)-5α-androst-1-ene, and pharmaceutically acceptable salts thereof.

4. The method of claim 1 wherein the subject is a female human.

5. The method of claim 1 wherein the compound of structural formula I is administered at a dose of 0.01 to 1000 mg per day.

6. The method of claim 1 wherein the compound of structural formula I is administered at a dose of 0.1 to 100 mg per day.

* * * * *